United States Patent [19]
Barr et al.

[11] Patent Number: 4,993,427
[45] Date of Patent: Feb. 19, 1991

[54] HEART CONTRACTION MONITOR

[75] Inventors: Howard S. Barr, Escondido; Joe E. Deavenport, San Diego; Robert J. Schuessler, Del Mar; Thomas A. Steinke, San Diego, all of Calif.

[73] Assignee: Sonotek Corporation, San Diego, Calif.

[21] Appl. No.: 434,136

[22] Filed: Nov. 9, 1989

[51] Int. Cl.⁵ ............................................... A61B 5/10
[52] U.S. Cl. ........................... 128/774; 128/661.07; 73/627
[58] Field of Search ............ 128/774, 661.07, 661.10, 128/721; 73/627, 379

[56] References Cited

U.S. PATENT DOCUMENTS

| | | | |
|---|---|---|---|
| Re. 32,782 | 11/1988 | Pratt, Jr. | 128/660.06 |
| 3,918,296 | 11/1975 | Kitada | 73/627 |
| 4,084,986 | 9/1977 | Ott | 128/2 R |
| 4,197,856 | 4/1980 | Northrop | 128/661.07 |
| 4,324,141 | 4/1982 | Stearn | 73/627 |
| 4,418,577 | 12/1983 | Arieh et al. | 128/774 |
| 4,571,750 | 2/1986 | Barry | 128/774 |
| 4,635,198 | 1/1987 | Hohlweck et al. | 364/414 |
| 4,653,505 | 3/1987 | Iinuma | 128/660 |
| 4,665,928 | 5/1987 | Linial et al. | 128/782 |
| 4,730,625 | 3/1988 | Fraser et al. | 128/781 |
| 4,732,038 | 3/1988 | DelGiorno et al. | 73/379 |
| 4,733,668 | 3/1988 | Torrence | 128/660 |
| 4,757,453 | 7/1988 | Nasiff | 364/415 |
| 4,774,959 | 10/1988 | Palmer et al. | 128/660.06 |
| 4,781,199 | 11/1988 | Hirama et al. | 128/660.01 |
| 4,805,636 | 2/1989 | Barry et al. | 128/774 |
| 4,947,854 | 8/1990 | Rabinovitz et al. | 128/662.06 |

Primary Examiner—Francis Jaworski
Assistant Examiner—George Manuel
Attorney, Agent, or Firm—Nydegger & Associates

[57] ABSTRACT

An apparatus for determining the magnitude of heart muscle contractions has two ultrasonic transceivers, both of which are disposed in sonic alignment on selected points of the heart. A digital counter electrically interconnects the transceivers with a digital microprocessor. The counter determines a pulse transit time which corresponds to the difference in time between the transmission of a sonic pulse from the transmitter and the reception of the sonic pulse by the receiver. Immediately after determining each pulse transit time, the counter sends the transit time signal to the microprocessor, which first filters the signals to reject any signal which indicates a heart size that is unreasonably large or small. After filtering, the transit times are averaged in groups of a predetermined number and then converted to corresponding heart size measurements for storage and display.

23 Claims, 2 Drawing Sheets

HEART CONTRACTION MONITOR

FIELD OF THE INVENTION

The present invention relates generally to apparatus for measuring muscle movement. More specifically, the present invention relates to signal processing of muscle contraction signals generated by a pair of transceivers which are disposed adjacent the muscle to be monitored. The present invention is particularly, though not exclusively, useful for measuring contractions of the heart muscle during or after cardiovascular surgery.

BACKGROUND OF THE INVENTION

It is well known that muscle contractions can be measured by attaching transducers to the muscle and detecting signals generated by the transducers that are proportional to the distance between the attachment points. One device that has been used for this purpose employs a transducer consisting of an elastic tube which is filled with conductive fluid. To operate this device, the ends of the tube are sutured in tension to the muscle whose displacement or contraction is to be measured. As the muscle moves, the length of the tube changes and, consequently, the electrical resistance of the tube also changes. Unfortunately, such a device has the disadvantage that it must be sutured to the muscle. Thus, it is not able to respond well to very small displacements, or to displacements which occur within a short period of time. In addition, such devices are more prone to cause injury or trauma to the muscle during their attachment and removal.

Another device, as disclosed in U.S. Pat. No. 3,937,212 to Fletcher et al., pertains to a miniature muscle displacement transducer. It senses muscle displacement or contraction utilizing a curved structural beam of high elastic compliance which is connected at its ends to two prongs. A sensitive strain gauge is bonded to the beam to generate an output that is directly related to changes in the beam curvature. As the muscle under observation expands and contracts, the prongs move and the beam curvature correspondingly experiences changes, which are detected by the strain gauge. No suturing is required with this apparatus. Instead, the pair of elongated prongs, which are oriented substantially parallel to one another and disposed in a plane which is substantially perpendicular to the plane of the curved beam, have sharp tips that are insertable into the muscle. The transducer must be fabricated and calibrated, however, to correlate its output signal changes as a function of changes in beam curvature. Moreover, it measures lateral contractions, and due to parallel positioning of the elongated probes, is not well suited to measure displacement between opposite sides of the muscle, such as is required when measuring the ventricular muscle of the heart.

It is also well known that ultrasonic transducers can be attached to a muscle to measure the variations in distance between the transducers as an indication of the muscle's movement and activity. Such ultrasonic transducers provide increased sensitivity, and can detect very small changes in the relative positions of the transducers within very small increments of time. Thus, ultrasonic transducers are able to provide an effective real-time representation of muscle activity. Unfortunately, conventional methods using such crystal ultrasonic transducers require the tranducers be sutured to the muscle to assure the transducers are properly held in place. In addition, the transducers must be properly aligned so the ultrasound energy is adequately focused between the transmitter and receiver to provide useful and accurate muscle activity information. Other transducers using sonomicrometry (e.g. piezoelectric crystals) to detect variations in heart muscle movement, have attempted to solve the problem of maintaining alignment of the crystal transducers. Some have used various shaped crystals which have larger beam widths and greater sensitivity with which to overcome any misalignment. These devices, however, still require implantation in the epicardium using a securing ring. Such a device is disclosed in the article entitled "An Improved Transducer for Measurement of Cardiac Dimensions with Sonomicrometry" by Trigt et al., *American Physiological Society,* 1981.

Yet another genre of transducer is disclosed in copending U.S. patent application Ser. No. 383,205, assigned to the same assignee as the present invention, which recognizes the need for a sonomicrometry system that can accurately measure heart contractions to monitor performance of the heart during cardiovascular surgery, and to warn immediately when a problem occurs. This invention provides for heart contraction monitoring without requiring suturing and prealignment of the transducers by attaching the sonic transducers to a transducer caliper for attachment to the heart muscle.

With specific regard to the heart muscle, the obvious desirability for relatively small sized transducers, unfortunately, is offset by the relatively low sound pressure levels produceable by these small transducers. Specifically, the generation and processing of meaningful electronic signals from low sound pressure levels is complicated. For example, the sound pressure level of the transmitted ultrasonic signal is on the order of one (1) microvolt. Furthermore, this signal undergoes significant attenuation as it crosses the heart and is occasionally undetected by the receiving transducer. Moreover, the detection problem is compounded by a relatively large amount of sonic background noise in the heart. Consequently, it is often the case that false detection signals are generated by the receiving transducer in response to noise, as opposed to a bona fide measurement transmission. These false signals are preferably rejected during the signal processing in order to present operators with more meaningful data. It will be understood, therefore, that given the inherent complexity of conditioning the relatively weak and often erratic heart measurement signals noted above, a signal processor is desired which can quickly perform relatively complicated signal processing of the signals generated by relatively small sized ultrasonic transducers. Relatively high degrees of processing speed and data flow rate are even more important in light of medically-based requirements for a high degree of heart size measurement accuracy, in addition to the requirement for a relatively large data flow. For example, it can be required that the transducer system suggested above produce 1000 heart size measurements per second, and that each measurement be accurate to within one-tenth of one millimeter. Accordingly, it will be understood that the speed and capacity of digital microprocessors make them attractive as signal processors for the kinds of sonomicrometry devices noted above.

In accordance with the discussion above, the present invention recognizes that a need exists to provide a heart contraction monitor which can process, store, and display a large number of measurements per unit time. The present invention also recognizes that a need exists to provide a heart contraction monitor which can recognize and reject heart size measurement signals that are unreasonably large or small. In addition, the present invention recognizes that a need exists to provide a heart contraction monitor which can control and monitor the pulsing of a sonic transducer system for measuring heart size. Finally, the present invention recognizes that a need exists to provide a heart contraction monitor which is relatively easy to operate and cost effective to manufacture.

SUMMARY OF THE INVENTION

An apparatus for determining the magnitude of heart muscle contractions comprises an ultrasonic transmitter and an ultrasonic receiver which are respectively positioned in sonic alignment at selected points on the surface of the heart muscle. The apparatus further comprises a microprocessor that is electronically connected to a counter and the counter, in turn, is electronically connected to both the ultrasonic transmitter and ultrasonic receiver. As intended here, the ultrasonic transmitter is used for generating a series of pulses of ultrasonic energy that are each sent from the transmitter, through the heart muscle, to the receiver. For each pulse transmission, the counter digitally measures the time it takes each pulse of ultrasonic energy to transit the heart muscle between the transmitter and the receiver.

These digitally measured pulse transit times are then electronically transferred from the counter to the microprocessor, where a plurality of sequential pulse transit times are summed during a predetermined sampling period. This sum is then averaged to generate a digitized signal which is representative of the distance between the transmitter and the receiver during the sampling period.

In order to evaluate and analyze the distance signals as indications of heart muscle contractions, the signals generated by the counter are transferred to the microprocessor. At the microprocessor, the signals are sequentially processed to create a time history of the distances between the transmitter and the receiver. This time history is electronically storable for archival purposes and is also presentable in selected segments to visually show the magnitude of the contractions of the heart muscle.

In order to use meaningful data for the generation of the muscle contraction time history, any obviously erroneous transit times which could greatly distort a distance signal are ignored by the microprocessor. Specifically, any transit times which would indicate a heart size that is, for example, in the range of twenty-five to thirty percent (25%-30%) greater, or lesser, than should be reasonably expected, are not used by the microprocessor in the generation of the distance signal. Further, in the event no usable transit times are received by the microprocessor during the sampling period, the distance signal for that sampling period is given an inherently meaningless value of zero.

As intended for the present invention, the ultrasonic transmitter is excited at a frequency of approximately one kilohertz (1 KHz). Thus, approximately one thousand (1000) pulses of ultrasonic energy transit the heart muscle between the transmitter and the receiver each second. Further, each distance signal is preferably generated using eight (8) sequential transit times. Consequently, approximately 7500 distance signals are generated each minute.

For the presentation of a muscle contraction time history using calculated data, the generated series of distance signals can be presented in a time sequence on either hard copy (i.e. paper) or on a liquid crystal display. Thus, sequential heart muscle contractions can be viewed over a preselected time interval (e.g. three seconds). Further, during each such time interval, the microprocessor is able to record and store the measured data pertaining to the maximum and minimum values of the distance obtained during signals the preselected time interval. With this data, long term trends for heart muscle contractions can be viewed and evaluated.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
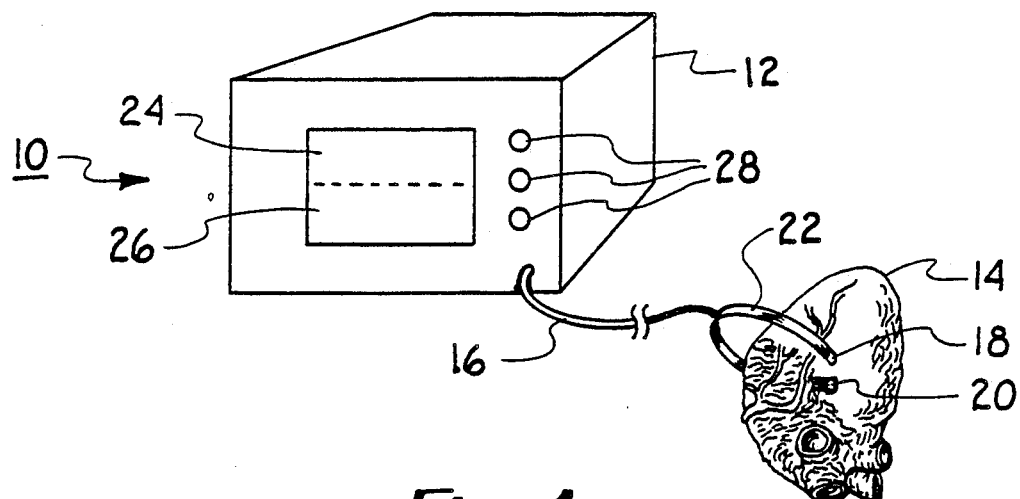
FIG. 1 is a perspective view of the housing and display console of the heart contraction monitor, showing the monitor electrically connected to a heart contraction sensor.

Referring initially to FIG. 1, a heart contraction monitor, generally designated 10, is shown covered by a housing 12 and electrically connected to a heart muscle 14 by transmission line 16. More particularly, transmission line 16 interconnects heart contraction monitor 10 with sonic transducer 18 and sonic transducer 20 (shown in phantom in FIG. 1) for signal processing as more fully disclosed below. As seen in FIG. 1, the present embodiment of heart contraction monitor 10 envisions transducers 18 and 20 being mounted in sonic alignment on an adjustable caliper 22. According to the desires of the operator, caliper 22 is positioned to hold both transducers 18, 20 in contact with heart muscle 14. Further details of the configuration and cooperation of the sonic caliper sensor system which comprises caliper 22 and transducers 18, 20 are disclosed in co-pending U.S. patent application Ser. No. 383,205, assigned to the same assignee as the present invention. It will be understood, however, that heart contraction monitor 10 may be used in conjunction with a wide variety of heart contraction sensors, such as strain gauge deflection sensors, without departing from the spirit and intent of the present invention. FIG. 1 also shows data display windows 24, 26, for displaying processed heart contraction data, and controls 28 for controlling the displays on windows 24, 26, and for energizing heart contraction monitor 10.

Figure 2:
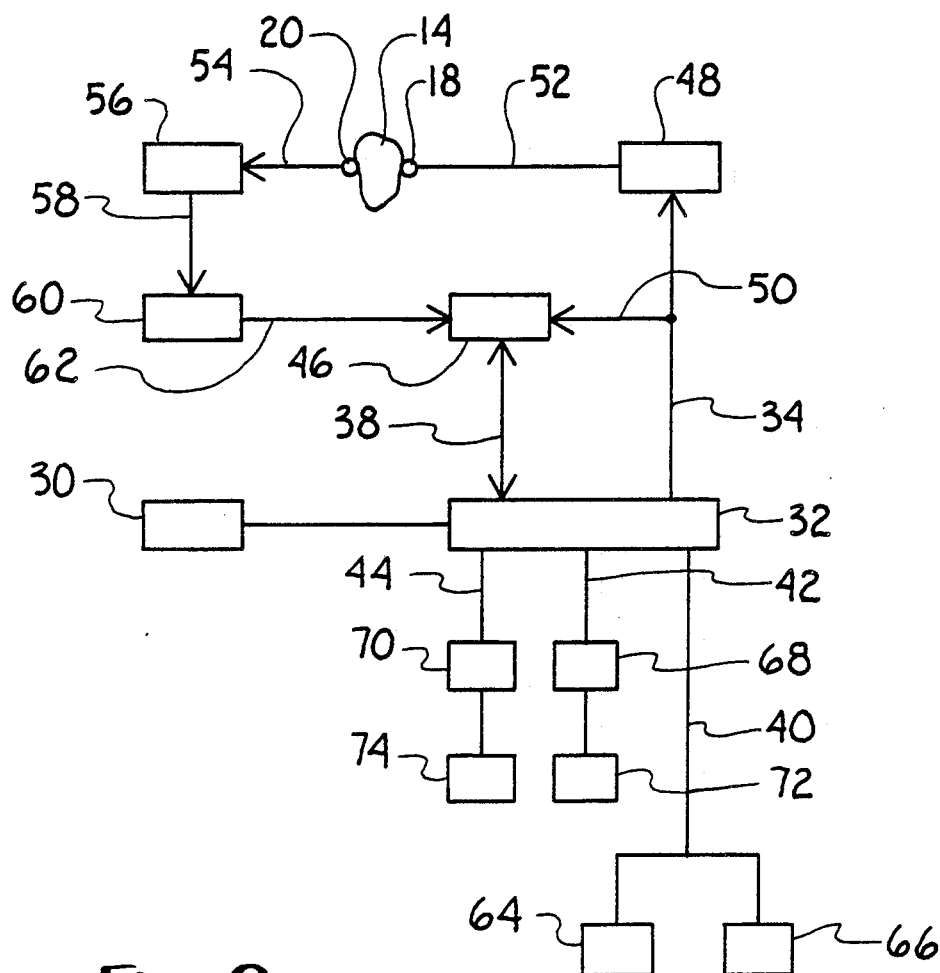
FIG. 2 is a schematic diagram of the digital components of the heart contraction monitor.

The details of the major electrical componentry of heart contraction monitor 10 are best seen in schematic in Figure 2. There, it will be seen that a combined digital micro processor/microcontroller 30 is electrically coupled to various other components of heart contraction monitor 10. In order to effectively perform the signal processing described below, microprocessor 30 should operate at a processing frequency of approximately ten (10) megaherz (Mhz), and preferably operate at a processing frequency of approximately twenty (20) Mhz.

As implied above, FIG. 2 shows microprocessor 30 electrically connected to several other components of heart contraction monitor 10 by a sixteen (16) bit data bus 32. While most of the data passed over data bus 32 requires only twelve (12) to fourteen (14) bits, it will be appreciated that capacity for future improvements in heart contraction measurement precision, as well as capacity to provide measurements of abnormally large hearts, is provided by a sixteen (16) bit data bus 32. Specifically, the skilled artisan will recognize that twelve (12) to fourteen (14) bit long data sets, representing a standard-sized heart muscle 14, are currently required in order to achieve a measurement for heart muscle 14 that is precise to within one-tenth (1/10) of one millimeter. More specifically, a standard-sized human heart has dimensions which are roughly in the range of thirty (30) to one hundred twenty (120) millimeters (mm). For applications requiring a heart size measurement that is accurate to within one-tenth (1/10) of one mm, it is therefore necessary to provide a data set which has a capacity to represent roughly one thousand to two thousand measurement divisions. As can be derived using sample mathematics, a twelve (12) to fourteen (14) bit long data set is capable of representing two to the twelfth ($2^{12}$) power to two to the fourteenth ($2^{14}$) power divisions of a single measurement, or four thousand ninety six (4096) to sixteen thousand three hundred eighty four (16384) divisions. Thus, a twelve (12) to fourteen (14) bit long data set has sufficient capacity to represent most standard sized heart measurments to within one tenth (1/10) of one mm. Accordingly, a sixteen (16) bit data bus provides capacity for more precise measurements of heart muscle 14, in addition to providing capacity to measure abnormally large heart muscles 14 or other relatively large muscles.

Shown connected to microprocessor 30 via line 38 is a digital counter 46, which records pulse transit times as more fully disclosed below. Also shown connected to microprocessor 30 via line 34 is a pulse generator 48, which generates electrical pulses that excite transducer 18 in response to control signals from microprocessor 30. In addition, counter 46 is itself connected to line 34 via line 50. It will therefore be appreciated that when microprocessor 30 sends a control signal to pulse generator 48 for transmission of a pulse by transducer 18, the control signal travelling over line 34 is also sent to counter 46 via line 50 to signal counter 46 to commence timing the pulse transit time. As indicated, pulse generator 48 is in turn electrically connected to transmitting transducer 18 via line 52 for electrically exciting transducer 18 to generate and direct an acoustic, or sonic, pulse through heart muscle 14 toward receiving transducer 20. Although not shown in FIG. 2, appropriate analog and digital signal conditioning electronics may be electrically interdisposed between pulse generator 48 and transducer 18 to properly condition the electrical pulse generated by pulse generator 48. While the electronic characteristics of the electrical pulse generated by pulse generator 48 will vary according to the requirements of the transducers 18, 20 and associated electronics, in the preferred embodiment of the present invention pulse generator 48 generates a square wave having an approximate amplitude in the range of one hundred thirty-five (135) to two hundred (200) volts and a duration in the approximate range of ten (10) to twenty (20) nanoseconds. When transducer 18 receives the electrical pulse, described above, generated by pulse generator 48, the crystals of piezoelectric transducer 18 are excited and are thereby induced to generate an acoustic pulse.

Upon propagation through heart muscle 14 of the acoustic wave pulse transmitted by transducer 18 in response to the pulse generation signal described above, receiving transducer 20, when properly disposed on heart muscle 14 in acoustic alignment with transducer 18, detects the acoustic pulse. Receiving piezoelectric transducer 20, in response to its detection of the acoustic pulse, in turn transmits an electrical detection signal. Stated differently, the electrical energy-to-acoustic energy transformation described above in regard to transducer 18 operation is reversed in the case of transducer 20 operation. The electrical detection signal generated by transducer 20 is transmitted across line 54 to analog conditioning circuitry 56. It will be appreciated that the function of analog conditioning circuitry 56 is to properly condition (i.e. amplify and smooth) the relatively small voltage signal generated by transducer 20, which is on the order of microvolts, for further processing. The conditioned signal is then sent via line 58 to comparator 60, which generates a square wave signal on line 62 in response to a properly-sized analog electrical signal on line 58. As seen in FIG. 2, the square wave receive signal on line 62 is conducted to counter 46, which signals counter 46 to stop timing the pulse transit time. Thus, counter 46 determines a pulse transit time across heart muscle 14, and sends this data set to microprocessor 30 via line 38. It will be appreciated that the resulting pulse transit time determined by counter 46 ignores electrical time delays which are external to the acoustic pulse transit time between transducers 18 and 20. It will be further appreciated, however, that these electrical delays are relatively insignificant compared to the acoustic delay between transducers 18, 20, and may therefore be ignored.

FIG. 2 also shows an external program read only memory (EPROM) device 64 and a random access memory (RAM) device 66 in electrical connection with microprocessor 30 via line 40. As is well known in the art, microprocessor 30 accesses EPROM 64 for executing program commands and RAM 66 for data storage and retrieval. As is further known in the art, EPROM 64 and RAM 66 may comprise portions of the physical embodiment of microprocessor 30. In addition, microprocessor 30 is electrically connected to liquid crystal interface board 68 and latches 70 via lines 42, 44, respectively. It will be appreciated that liquid crystal interface board 68 drives data display 72 which, in the present embodiment, is a liquid crystal display. Similarly, latches 70 provide parallel information for hard copy display 74, which may comprise any appropriate printing device. It will be recognized by those skilled in the art, however, that any suitable means for displaying data processed by microprocessor 30 may be incorporated into heart contraction monitor 10 without departing from the scope and intent of the present invention.

OPERATION

Figure 4:
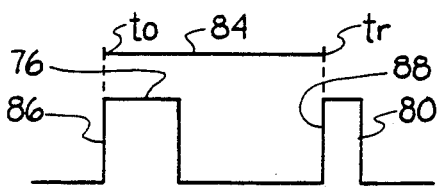
FIG. 4 is a schematic waveform diagram of the digitized transmit and receive signals of the heart contraction monitor.

In the operation of heart contraction monitor 10, reference is initially made to FIGS. 2 and 4. To initiate a heart contraction measurement pulse, microprocessor 30, shown in FIG. 2, sends a pulse generator command 76, shown schematically in FIG. 4, to pulse generator 48. This command signal 76 is also conducted to pulse counter 46, which begins timing the transit of the generated pulse, represented by $t_0$ In order to provide for a sufficiently large number of data points per unit time, microprocessor 30 commands pulse generator 48 to initiate a pulse approximately one thousand (1000) times per second, although greater or lesser pulse generation frequencies may be used. Now referring to FIG. 2, upon receiving the pulse command from microprocessor 30, pulse generator 48 generates an electrical square wave which is sent via line 52 to transmitting transducer 18. Transducer 18 transforms the electrical pulse from pulse generator 48 into a sonic, or acoustic, pulse, which is directed into heart muscle 14. Upon propagation of the sonic pulse through heart muscle 14, receiving transducer 20, when properly aligned with transmitting transducer 18, detects the sonic pulse and transforms the received sonic pulse into an electrical signal. This electrical signal is then conditioned by conditioning circuitry 56 and is subsequently passed to comparator 60. Upon receipt of a properly conditioned (i.e., properly shaped and amplified) signal from circuitry 56, comparator 60 generates a square response wave 80, shown in schematic in FIG. 4, and transmits this signal to counter 46. Counter 46 stops timing the transit of the pulse at ($t_r$) of square wave 80 to thereby determine a pulse transit time 84. In particular, as seen in FIG. 4, pulse transit time 84 is the time delay, as sensed by counter 46, between the leading edge 86 of pulse command wave 76 and leading edge 88 of square response wave 80. Once counter 46 computes pulse transit time 84, pulse transit time 84 is sent to microprocessor 30 for processing as described below.

Figure 3:
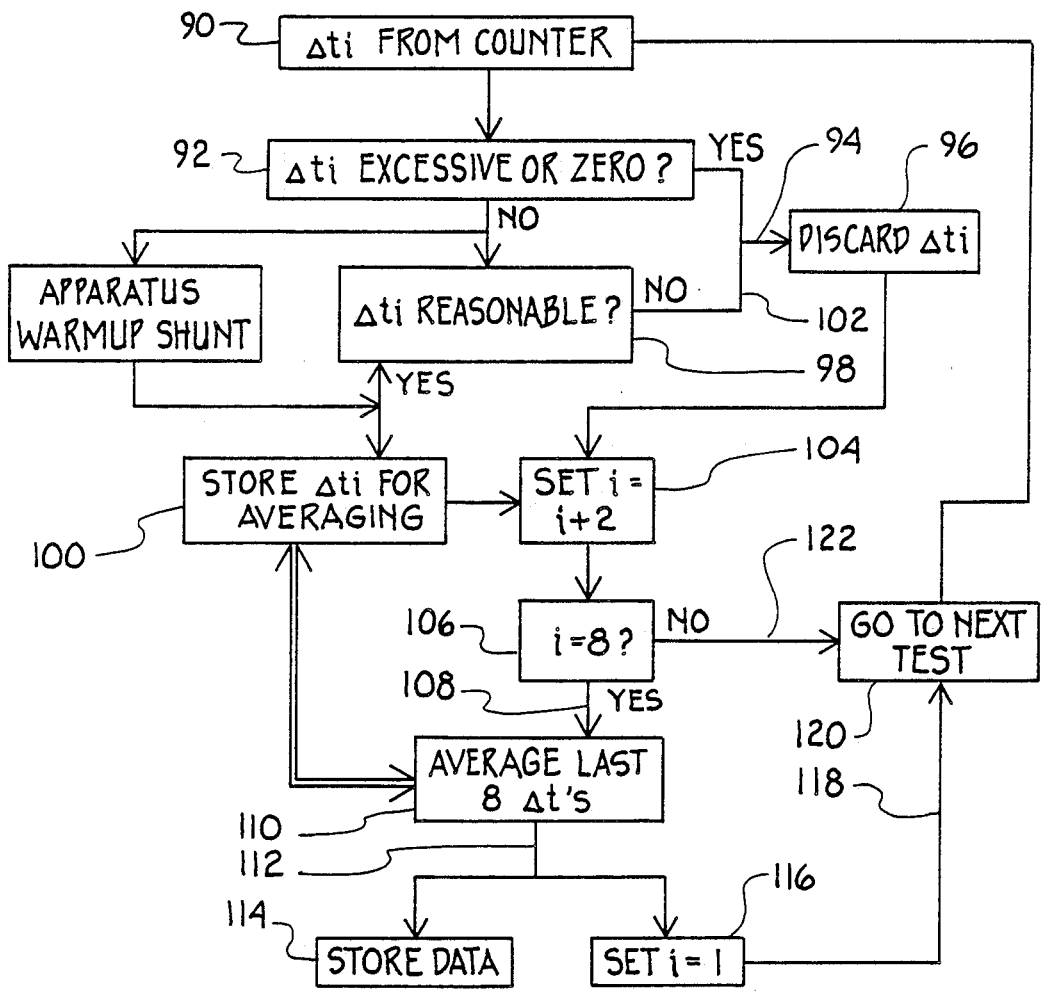
FIG. 3 is a logic tree which represents a portion of the logic used by the heart contraction monitor for processing heart contraction signals.

The signal processing performed by microprocessor 30 on pulse transit times 84 is best appreciated with reference to FIG. 3. In FIG. 3, pulse transit time 84 is denoted $t_i$; with subscript i denoting the temporal sequence of the particular pulse transit time 84 under test. The logic processing loop of microprocessor 30 may be seen to begin at block 90, where microprocessor 30 receives pulse transit time 84 from counter 46. Next, microprocessor 30 determines whether pulse transit time 84 is excessively long (i.e., approaching or exceeding sixteen (16) bits in length) or excessively short (i.e., a zero value) at block 92. Specifically, a normally sized heart muscle 14 typically is of a dimension that will require approximately twelve (12) to fourteen (14) bits of data to represent, depending on the required degree of measurement precision. Therefore, a pulse transit time 84 data set which significantly exceeds or falls short of 12-14 bits in length is discounted, or rejected, and is processed across line 94 to discard block 96. On the other hand, for pulse transit times 84 which are not plainly erroneous as determined at block 92, microprocessor 30 performs a second determination to assess the relative reasonableness of the particular pulse transit time 84 under test. To perform this second test, microprocessor 30 compares the particular pulse transit time 84 under test to the immediately precedent pulse transit time 84 that has not been discarded, or rejected, at blocks 92 or 98. Specifically, as seen in FIG. 3, microprocessor 30 performs the operation described above at block 98 by accessing immediate storage block 100, which stores a plurality of the non-discarded temporally precedent pulse transit times 84. Microprocessor 30 retrieves for comparison the pulse transit time 84 which is immediately precedent to the pulse transit time 84 under test. Microprocessor 30 then performs the comparison described above and, if the current pulse transit time 84 exceeds or falls short of the immediately precedent pulse transmission time 84 by a predetermined amount, the current pulse transmission time 84 is discarded through lines 102 and 94 to discard box 96. As those skilled in the art will recognize, the logic underlying the microprocessor 30 comparison at block 98 is that the heart muscle 14 cannot undergo a relatively instantaneous change in size which is of a relatively large magnitude. Thus, any pulse transit time 84 which indicates an unrealistically large instantaneous change of size of heart muscle 14 may be considered to be a false signal. While the present invention contemplates the use of a wide range of other predetermined values for rejecting such false pulse transit times 84 may be used, the present invention rejects at block 98 any pulse transit times 84 which are approximately thirty (30) per cent greater or lesser than the immediately precedent pulse transit time 84.

If pulse transit time 84 passes both the block 92 and block 98 tests, it is stored for temporary referral at block 100. Then, regardless whether pulse transit time 84 has been rejected or accepted, microprocessor 30 resets the i value to i + 1 at block 104 and determines if now-reset i is an integer multiple of eight (8), at block 106. As seen in FIG. 3, if i is an integer multiple of eight (8), microproccessor 30 proceeds along line 108 to average the most recent eight (8) pulse transmission times 84 at block 110. It will therefore be understood that while a wide size range of pulse transit time 84 data sets may be selected for averaging, the present invention averages the eight most recent pulse transit times 84 in order to present more meaningful data to the operators of heart contraction monitor 10. Moreover, microprocessor 30 may be programmed to average the eight most recent pulse transit times 84 which have passed the tests at blocks 92 and 98, or average the eight most recent pulse transit times 84 regardless of whether the times 84 have been rejected or accepted. In the latter case, it will be understood that when the averaged group contains one or more rejected data sets, the rejected data set will be ignored and the effective group size for averaging will be decreased accordingly. After averaging at block 110, the now-averaged data set comprising up to eight (8) individual pulse transit times 84 is passed along line 112 to be stored in RAM 66, the storage process taking place at block 114. In addition, the now-averaged data set is sent to block 116 to signal microprocessor 30 to reset the i value to one (1). The microprocessor 30 logic then proceeds along line 118 to block 120, which signals microprocessor 30 to continue to block 90 and to standby for the processing of subsequent pulse transit times 84. On the other hand, for those cases wherein now reset i at block 106 is not an integer multiple of 8, microprocessor 30 immediately proceeds along line 122 to block 120, and thence returns to block 90 in standby for the testing of subsequent pulse transit times 84. It will therefore be appreciated that independent of the number of pulse transit times 84 actually averaged by microprocessor 30, microprocessor 30 proceeds to store and average the next set of eight (8) pulse transit times when i is reset to unity.

Figure 5:
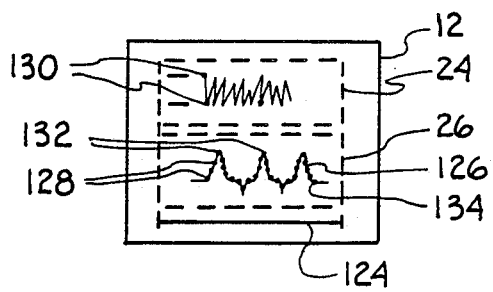
FIG. 5 is a notional data display generated by the heart contraction monitor, with pixel sizes exaggerated for clarity.

Regarding the particular provisions for data display of heart contraction monitor 10, reference is made to FIG. 5. While various displays may be designed which can effectively present the data as processed according to the foregoing disclosure, the present embodiment of monitor 10 envisions both a short time averaged (STA) display window 26 and a long time averaged (LTA) display window 24, as shown in FIG. 5. In particular, STA window 26 displays approximately the three most recent seconds of averaged data which have been generated by microprocessor 30 (see block 110 in FIG. 3) and subsequently converted to a corresponding distance signal by microprocessor 30. It will be recalled that each data set generated at block 110 comprises the average of eight (8) individual pulse transit times 84, which are in turn generated by counter 46 one thousand (1000) times per second. Thus, it will be understood that one hundred twenty five (125) averaged data sets are generated by microprocessor 30 at block 110 each second. In accordance with the above discussion, then, width 124 of STA display 26, in the present embodiment, is at least three times one hundred twenty five (3×125) pixels wide, or three hundred seventy five (375) pixels. Referring now to FIG. 5, three-second curve 126 of STA display 26 is seen to be comprised of a plurality of pixels 128, each of which represents a single averaged data set generated by microprocessor 30 at block 110. It will therefore be appreciated, in cross-reference to FIGS. 2 and 5, that three second curve 126 is updated by microprocessor 30 through liquid crystal counter 68 one hundred twenty five (125) times per second. In addition to driving three second curve 126 as disclosed above, microprocessor 30 also generates and updates the data presented on LTA display 24. Specifically, each pixel 130 of LTA display 24 corresponds to a peak maximum 132 or minimum 134 of three second curve 126. Moreover, heart contraction monitor 10 provides for operator shifting of the time period encompassed by LTA display 24. For example, one of the control knobs 28 shown in FIG. 1 may be interconnected to microprocessor 30 and LTA display 24 to selectively display data as disclosed above for the most recent one, two, four, eight, or sixteen hour monitoring period. To this end, it will now be appreciated that RAM 66, shown in schematic in FIG. 2, maintains and updates tables of averaged pulse transit time 84 data sets, the size of which tables correspond to available time period selections for STA display 24 and LTA display 26.

While the particular muscle contraction monitor as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. An apparatus for dynamically determining the dimension of a muscle which comprises:
    means for transmitting a sonic or ultrasonic pulse into said muscle through a first surface of said muscle at a first time;
    means for receiving and signalling the emergence of said pulse from a second surface of said muscle opposite said first surface of said muscle at a second time;
    means for determining the difference between said first time and said second time to generate a pulse transmit time;
    processing means for filtering said pulse transit time and ignoring said pulse transit time when said pulse transit time is not within a predetermined range; and
    means for converting said pulse transit time to a distance signal for display and storage.

2. An apparatus for dynamically determining the dimension of a muscle as recited in claim 1 wherein said transmitting and receiving means comprise ultrasonic transducers and associated pulse amplification and pulse shaping electronic components.

3. An apparatus for dynamically determining the dimension of a muscle as recited in claim 1 wherein said timing means comprises a digital counter.

4. An apparatus for dynamically determining the dimension of a muscle as recited in claim 1 wherein said processing means comprises a digital microprocessor.

5. An apparatus for dynamically determining the dimension of a muscle as recited in claim 1 wherein said transmitting means transmits a plurality of said pulses, said pulses being sequentially separated, each of said pulses being transmitted at a respective first time and received at a respective second time for generating respectively sequential pulse transit times.

6. An apparatus for dynamically determining the dimension of a muscle as recited in claim 5 wherein said predetermined range is determined to be bonded between thirty (30) percent greater and thirty (30) percent lesser than a predetermined time.

7. An apparatus for dynamically determining the dimension of a muscle as recited in claim 6 wherein said predetermined time is determined individually for each of said pulse transit times to be the temporally precedent transit time.

8. An apparatus for dynamically determining the dimension of a muscle as recited in claim 7, wherein said muscle is a contracting heart muscle and wherein said timing means further comprising comparison means coupled between said timing means and said receiving means for generating a digital pulsed signal to said timing means whenever said sonic pulse signal appearing at said receiving means exceeds a preselected level.

9. An apparatus for dynamically determining the magnitude of a muscle as recited in claim 5, wherein said muscle is a contacting heart muscle and wherein said distance signals comprise the converted average of eight (8) of said pulse transit times.

10. An apparatus for measuring the variations of a muscle's size, over time, which comprises:
    means for generating sonic pulses through said muscle;
    means for receiving and signalling the reception of said pulses after said pulses transit said muscle;
    timing means for determining the transit times of said pulses through said muscle;
    processing means for filtering said transit times and rejecting said transit times which exceed a predetermined value;
    means for averaging the remaining transit times; and
    means for converting said averaged transit times to distance signals for display and storage.

11. An apparatus for measuring the variations of a muscle's size, over time, as recited in claim 10 wherein said generating and said receiving means comprise ultrasonic transducers and associated pulse amplification and pulse shaping electronic components.

12. An apparatus for measuring the variations of a muscle's size, over time, as recited in claim 10 wherein said timing means comprises a digital counter.

13. An apparatus for measuring the variations of a muscle's size, over time, as recited in claim 10 wherein said processing means comprises a digital microprocessor.

14. An apparatus for measuring the variations of a muscle's size, over time, as recited in claim 10 wherein said predetermined value is determined to be thirty (30) percent greater or lesser than a predetermined time.

15. An apparatus for measuring the variations of a muscle's size, over time, as recited in claim 14 wherein said predetermined time is determined individually for each of said transit times to be the temporally precedent transit time.

16. An apparatus for measuring the variations of a muscle's size, over time, as recited in claim 15 wherein said timing means further comprise comparison means coupled between said timing means and said receiving means for generating a digital pulsed signal to said timing means whenever said emergent pulse signal from said receiving means exceeds a predetermined value.

17. An apparatus for measuring the variations of a muscle's size, over time, as recited in claim 10 wherein said distance signals comprise the converted average of eight (8) of said transit times.

18. A method for measuring the variations in a muscle's size, over time, comprising the steps of:
transmitting sonic pulses into said muscle;
receiving said pulses;
signalling the reception of said pulses after said pulses transit said muscle;
determining the length of time of said pulse transit through said muscle;
rejecting said transit times which exceed a predetermined value;
averaging said transit times; and converting said averaged transit times to distances.

19. A method for measuring the variations in a muscle's size, over time, as recited in claim 18 further comprising the step of storing and displaying said distances.

20. A method for measuring the variations in a muscle's size, over time, as recited in claim 18 wherein said predetermined value is determined to be thirty (30) per cent greater or lesser than a predetermined transit time.

21. A method for measuring the variations in a muscle's size, over time, as recited in claim 20 wherein said predetermined transit time is determined individually for each of said transit times to be the temporally precedent transit time.

22. A method for measuring the variations in a muscle's size, over time, as recited in claim 18 further comprising the step of generating a digital pulsed signal for determining said transit time whenever said pulse reception signal exceeds a predetermined value.

23. A method for measuring the variations in a muscle's size, over time, as recited in claim 18 wherein said averaging step comprises averaging eight (8) sequential transit times.

* * * * *